(12) United States Patent
Heimbigner

(10) Patent No.: US 10,470,507 B2
(45) Date of Patent: Nov. 12, 2019

(54) BIRTHING ARTICLE OF APPAREL

(71) Applicant: Pullman Regional Hospital, Pullman, WA (US)

(72) Inventor: LaurelLee Heimbigner, Pullman, WA (US)

(73) Assignee: Pullman Regional Hospital, Pullman, WA (US)

( * ) Notice: Subject to any disclaimer, the term of this patent is extended or adjusted under 35 U.S.C. 154(b) by 228 days.

(21) Appl. No.: 15/477,331

(22) Filed: Apr. 3, 2017

(65) Prior Publication Data

US 2018/0279698 A1   Oct. 4, 2018

(51) Int. Cl.
| | | |
|---|---|---|
| *A41D 3/08* | (2006.01) | |
| *A41D 13/12* | (2006.01) | |
| *A41D 1/21* | (2018.01) | |
| *A61B 5/00* | (2006.01) | |

(52) U.S. Cl.
CPC ........... *A41D 13/1281* (2013.01); *A41D 1/21* (2018.01); *A41D 3/08* (2013.01); *A41D 13/1245* (2013.01); *A41D 13/1254* (2013.01); *A41D 2400/38* (2013.01); *A61B 5/4356* (2013.01); *A61B 5/6804* (2013.01)

(58) Field of Classification Search
CPC .............. A41D 13/1281; A41D 13/129; A41D 13/1254; A41D 13/1236; A41D 1/21; A41D 15/02; A41D 15/04; A41D 1/215; A41D 1/22; A41D 1/16; A41D 1/18
USPC .............................................................. 2/88
See application file for complete search history.

(56) References Cited

U.S. PATENT DOCUMENTS

| 1,003,734 | A | | 9/1911 | Goldberg | |
|---|---|---|---|---|---|
| 1,119,136 | A | | 12/1914 | Cohn | |
| 1,886,049 | A | * | 11/1932 | Rothblum | A41D 7/00 2/67 |
| 2,255,697 | A | | 9/1941 | Cohn | |
| 2,722,011 | A | * | 11/1955 | Maines | A41D 1/21 2/76 |
| 4,663,782 | A | * | 5/1987 | Knox | A41D 1/215 2/104 |
| 5,461,725 | A | * | 10/1995 | Witczak | A41D 1/215 2/104 |
| 5,717,998 | A | * | 2/1998 | Everett | A41D 7/00 2/408 |

(Continued)

FOREIGN PATENT DOCUMENTS

JP   2011252263   12/2011

OTHER PUBLICATIONS

Angie, "The Pros and Cons of Knit and Woven", Retrieved on May 8, 2018 from https:l/youlookfab.com/2008/08/27 / the-pros-and-cons-of-knits-and-wovens/>, 14 pages.

(Continued)

*Primary Examiner* — Timothy K Trieu
(74) *Attorney, Agent, or Firm* — Lee & Hayes, P.C.

(57) ABSTRACT

An article of apparel includes a birthing skirt. The birthing skirt includes a skirt portion having a waist opening, and a tubular portion having an end attached to the waist opening of the skirt portion. A material of the tubular portion includes a shape-conforming, elastic material. A pocketless aperture is through a side of the birthing skirt and is sized to accommodate a width of at least one of a fetal monitor transducer, a contraction monitor transducer, or a cable of a monitor transducer.

14 Claims, 3 Drawing Sheets

(56) References Cited

U.S. PATENT DOCUMENTS

| | | | |
|---|---|---|---|
| 6,185,741 B1 * | 2/2001 | Kehoe | A41D 7/00 2/67 |
| 6,206,005 B1 | 3/2001 | Keyes | |
| 6,327,712 B1 * | 12/2001 | Armstrong | A41D 1/215 2/104 |
| 7,181,773 B1 * | 2/2007 | Piraka | A41D 13/1281 2/114 |
| 8,051,496 B2 * | 11/2011 | Hersh | A41D 7/00 2/67 |
| 9,101,169 B1 | 8/2015 | Leach | |
| 2006/0179540 A1 * | 8/2006 | Rotter | A41D 1/21 2/114 |
| 2008/0000004 A1 * | 1/2008 | Lucock | A41D 1/215 2/104 |
| 2010/0017929 A1 * | 1/2010 | Kenney | A41D 13/04 2/49.1 |
| 2010/0299797 A1 | 12/2010 | Riehl | |
| 2012/0030858 A1 * | 2/2012 | Duffin | A42B 3/0406 2/183 |

OTHER PUBLICATIONS

The PCT Search Report and Written Opinion dated Aug. 28, 2018, for PCT Application No. PCT/US18/25943, 9 pages.

* cited by examiner

BIRTHING ARTICLE OF APPAREL

BACKGROUND

Hospital gowns in general are notoriously inadequate for preserving any semblance of privacy for a patient. Regardless of the reason for the hospital stay, it seems that the gowns offered to patients constantly overexpose the patients unnecessarily. While some hospital departments may have used a variety of gowns that are more specific to the actions that occur frequently in those departments, the continual common complaint is still that the gowns make the patients feel extremely exposed.

In the labor and delivery department, the gowns typically used may include a way for the birthing mother wearing the gown to easily access her breasts immediately after the delivery so that the newborn baby can have skin to skin contact and begin to try to nurse. While the concept of a do-it-all gown that works for labor, delivery, and post-delivery is a practical solution, the minor changes between the variety of obstetric gowns still fail to provide the one thing that most women have simply accepted as an impossibility in the situation, which is a little more privacy and modesty.

One problem with the presence of a gown during labor and delivery is the need to periodically, and sometimes frequently, adjust the positions of fetal and contraction monitor transducers over the mother's abdomen. To accommodate for transducer adjustments, the delivery, and post-delivery, generally, the gown is pushed up to waist level or higher in order to make the adjustment, check the labor progress, or deliver the baby. Thus, conventional obstetric gowns used by women during labor and delivery may have a split down the back and/or front, may wrap around the torso loosely, may have gaping openings for breast access, may have openings too small for an average woman to access her breasts, may precariously unsnap at the shoulder and then expose the entire breast, or may require frequent undoing and redoing of string ties in order to maintain a sense of privacy, etc.

Additionally, a common complaint is simply that the gowns are ugly. This complaint may be related to some extent to the fact that many gowns are fit for a one-size-fits-all type of use. As such, for smaller women, the gowns may have too much material to manage without being overexposed, and for larger women, the gowns may not have enough material, and they cannot help but be overexposed. Accordingly, a better option of apparel is desired for obstetric gowns.

BRIEF DESCRIPTION OF THE DRAWINGS

The Detailed Description is set forth with reference to the accompanying figures. In the figures, the left-most digit(s) of a reference number identifies the figure in which the reference number first appears. The use of the same reference numbers in different figures indicates similar or identical items. Furthermore, the drawings may be considered as providing an approximate depiction of the relative sizes of the individual components within individual figures. However, the drawings are not to scale, and the relative sizes of the individual components, both within individual figures and between the different figures, may vary from what is depicted. In particular, some of the figures may depict components as a certain size or shape, while other figures may depict the same components on a larger scale or differently shaped for the sake of clarity.

DETAILED DESCRIPTION

Overview

This disclosure is directed to an article of apparel. More specifically, the description and associated figures of this application relate to apparel particularly well-suited for use by a pregnant woman preparing to deliver a child, whether in a hospital setting or otherwise. While the article of apparel may certainly be used in other settings and under other circumstances, various aspects and features of the apparel as described herein may provide advantages to a user who is going through the labor and delivery process.

For many years, hospital obstetric gowns have been a single piece, unsupportive, and often inconvenient, robe-like garment that is intended to allow quick access to the user's chest and groin regions for monitoring, delivering, and nursing a new baby. Several concerns and annoyances accompany such single-piece gowns, for both the user and the medical attendants involved in the care of the woman giving birth. For example, fetal monitor transducers and contraction monitor transducers are frequently placed directly on the skin of the pregnant abdomen to track the stability of the unborn child and the progress of the labor, respectively. To place the transducers properly, the gown is pushed or pulled aside from the lower abdomen. However, due to the nature of the single-piece conventional gown, the exposure of the abdomen almost invariably also exposes at least one or both of the woman's groin region or chest region unnecessarily. After placing the transducers, the gown may be moved back into position to cover the woman's body. Unfortunately, due to movement of the baby while in the womb and/or the mother while shifting position for comfort, the transducers may shift out of place or need to be readjusted to reacquire accurate readings. While minor adjustments may sometimes be made through the material of the gown, frequently it is necessary to move the gown again and re-expose the woman.

Although birthing mothers are aware that ultimately their bodies will end up quite exposed to deliver the baby, many women still have a desire to maintain some sense of privacy and decency by limiting exposure as much as possible prior to the actual delivery. This is particularly true when a woman may have visitors in the room with whom she is uncomfortable seeing her body exposed.

Accordingly, the article of apparel described herein may address some of the concerns discussed above by providing a form-fitting and functional alternative to the conventional gown.

Illustrative Embodiments of a Birthing Article of Apparel

Figure 1:
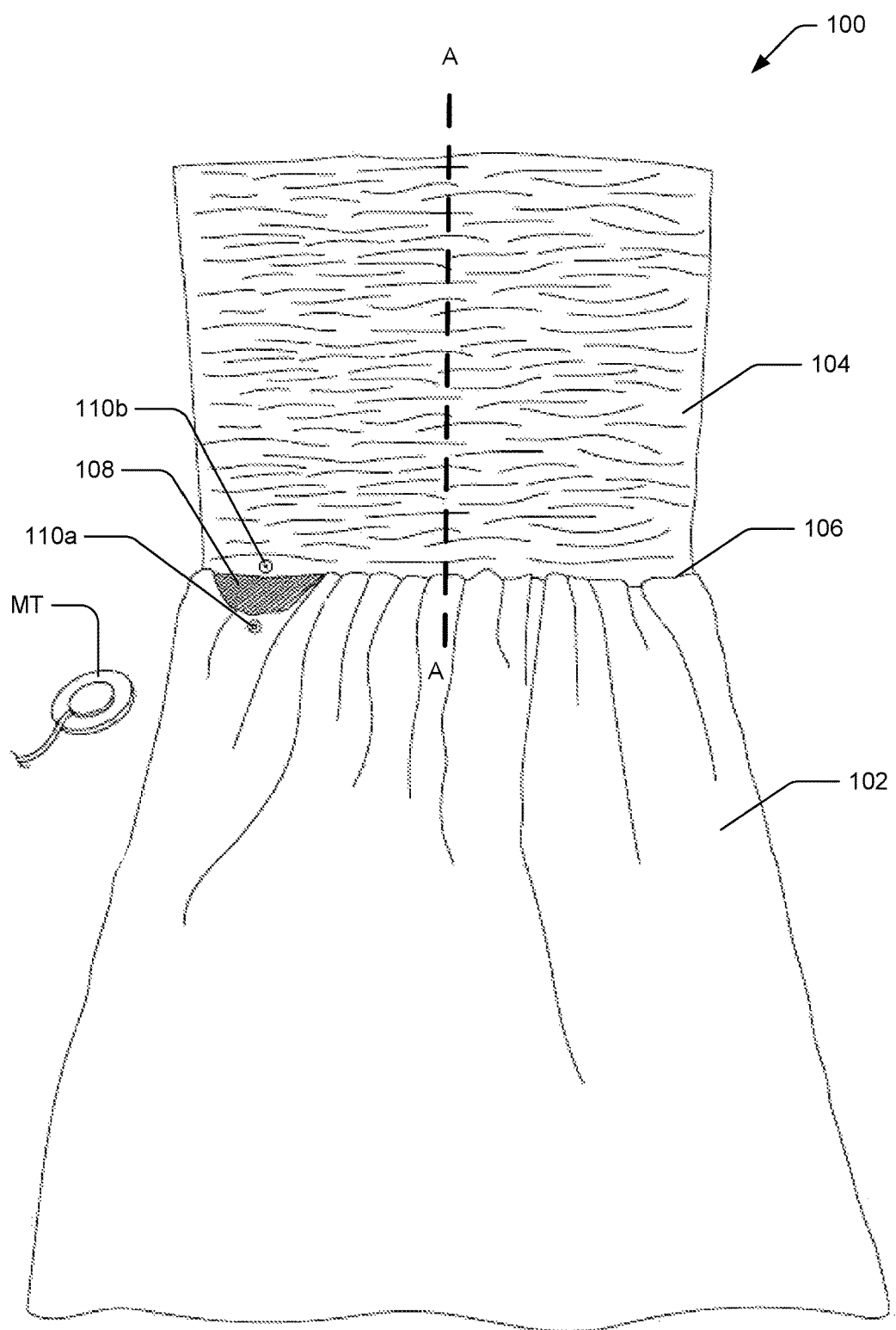
FIG. 1 illustrates a birthing skirt according to an embodiment of the instant application.

FIG. 1 depicts a birthing skirt 100 that may be worn by a pregnant woman throughout labor and delivery. Birthing skirt 100 may further be worn post-delivery as features of birthing skirt 100 may assist in the post-delivery events (e.g., evacuation of the uterus). Birthing skirt 100 may include a skirt portion 102 attached to a tubular portion 104. Tubular portion 104 is formed to slide and snugly fit over the pregnant woman's abdomen so that skirt portion 102 rests over the groin area and legs. As privacy and decency are desirable, a length of skirt portion 102 may extend to cover a portion of the woman's lower body, for example, to a knee of a user. Such length, of course, would depend on the body structure and length of the user. However, a statistical average length of a mature woman's body may be used to determine a length of skirt portion 102. An additional factor for consideration with respect to the length of skirt portion 102 may be the amount of material that would be pushed up out of the delivery path at the time of delivery. In other words, one might consider whether the length of skirt portion 102 is so long that the amount of material hinders the process of delivering the baby. Additionally, one may further consider whether the length of skirt portion 102 is so short that privacy is essentially eliminated. Therefore, the length of skirt portion 102 may vary.

The material from which skirt portion 102 is formed may vary as well. In an embodiment to accommodate patients who may be allergic to latex, a latex-free material may be used for skirt portion 102. Moreover, in view of a goal for privacy while avoiding hindering the delivery, a lightweight, opaque, thin material may be implemented. For example, the thin cotton or cotton-based materials currently used in many medical gowns may be used. Additionally, and/or alternatively, skirt portion 102 may be formed of a material that is more commonly considered to be a "disposable" material, such as a paper-based material (e.g., cellulose fabric). In yet another embodiment, skirt portion 102 may be formed of a knit material, which may provide additional warmth. Thus, skirt portion 102 may be formed from any suitable material as desired. Indeed, the material of skirt portion 102 may be reusable and washable or it may be disposable for sanitation purposes.

Skirt portion 102 may be connected to tubular portion 104 along a waist opening 106 of skirt portion 102. Waist opening 106 may include an elastic material to accommodate various sizes of women. Thus, skirt portion 102 may gather together to some extent at waist opening 106, and may stretch and ungather when worn by a user. Likewise, tubular portion 104 may gather together at waist opening 106 with skirt portion 102 and stretch when worn. Thus, a seam (i.e., union, whether continuous or intermittent) may be formed between tubular portion 104 and skirt portion 102 at waist opening 106. In an embodiment, the seam may be a threaded seam by sewing tubular portion 104 and skirt portion 102 together at least partially. Additionally, and/or alternatively, the seam may be formed via adhesion or any of a variety of mechanical fasteners. For example, an adhesive such as a medical grade resin or glue may be used to attach tubular portion 104 and skirt portion 102. In another example of adhesion, depending the materials used for tubular portion 104 and skirt portion 102, heat may be applied to form a bond between the materials, thereby forming a seam. Some examples of mechanical fasteners may include: button snaps, zippers, hook and loop material fasteners, buttons and buttonholes, lace ties, etc.

Tubular portion 104 may include a material that is elastic, so as to stretch and be shape-conforming against the woman's abdomen throughout all phases of the labor and delivery. In an embodiment, the material of tubular portion 104 may include a combination of nylon and spandex, which stretches to conform to the shape of the body. Other elastic materials may be implemented as well. The length of tubular portion 104 may vary so as to cover all or a portion of the woman's pregnant abdomen. For example, tubular portion 104 may be sized to extend from the top of a user's abdomen just below the user's breasts to the bottom of the user's abdomen just above or at the user's groin. In an embodiment, tubular portion 104 has a length that covers the abdomen to the extent that a monitor transducer M, such as a fetal monitor transducer or a contraction monitor transducer, may be held in place on the abdomen skin by positioning monitor transducer MT beneath tubular portion 104. Furthermore, tubular portion 104 may be formed as a unitary tubular shape or as a strip of fabric having opposite ends of the strip connect via mechanical fasteners to form a tubular shape when fastened, which may facilitate a woman in getting dressed in birthing skirt 100. Though the embodiment of tubular portion 104 (and similarly a tubular section of a birthing garment top described later herein) being formed as a strip of fabric with reconnectable opposing ends to form the tubular shape, is not explicitly depicted, line A-A in FIG. 1 indicates the location of where tubular portion 104 might be separated to allow for such an embodiment.

Figure 3:
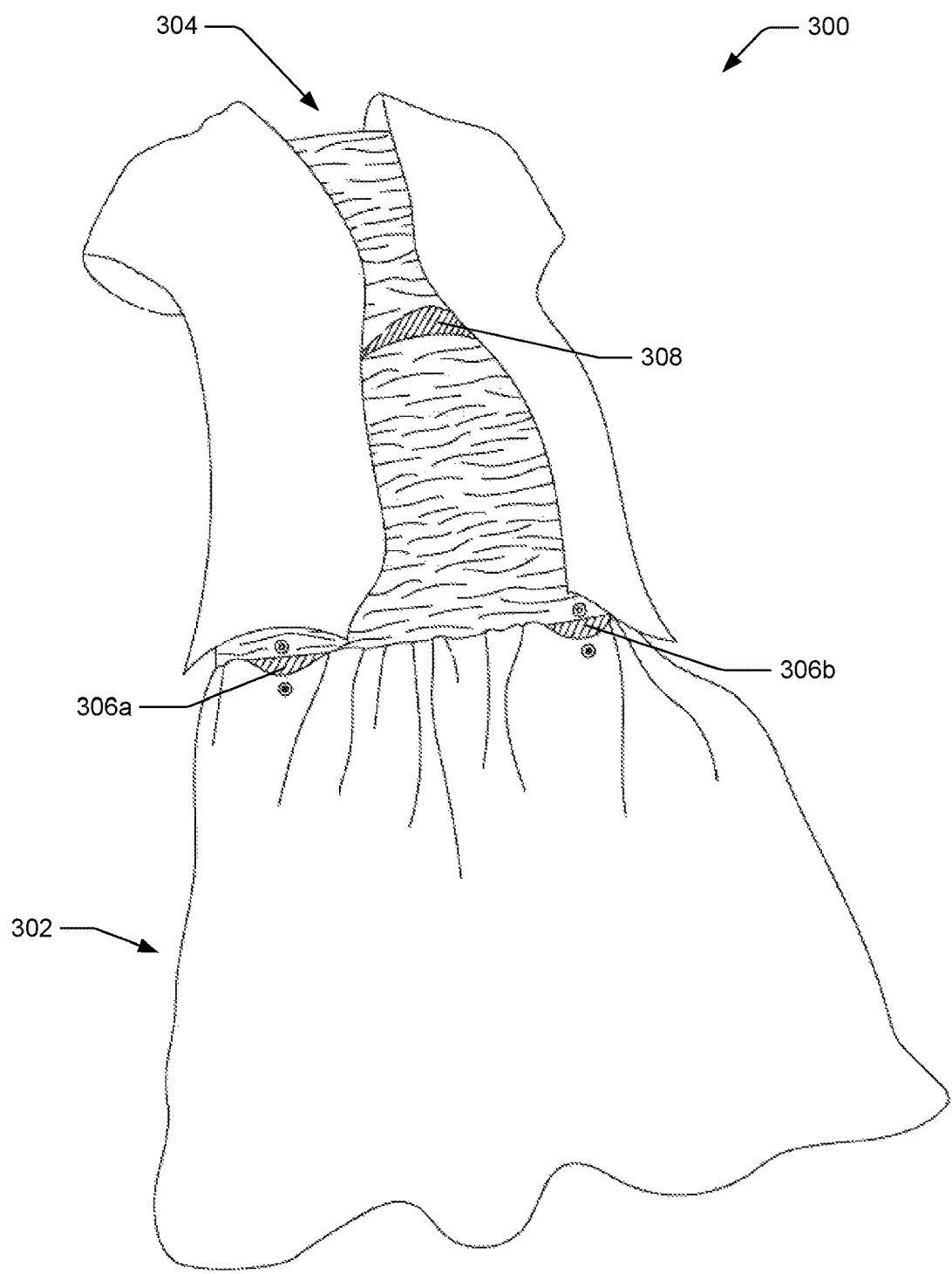
FIG. 3 illustrates a birthing skirt and birthing garment top according to an embodiment of the instant application.

Birthing skirt 100 may further include one or more pocketless apertures 108 (e.g., slit) through the side of birthing skirt 100 (only one pictured in FIG. 1, see FIG. 3 for two). The one or more pocketless apertures 108 may be sized to accommodate a greatest width of at least one of a fetal monitor transducer, a contraction monitor transducer, or a cable of the fetal monitor transducer and/or the contraction monitor transducer, or any other monitor transducer that may be used during the birthing process, so as to allow the monitor transducer MT or cable thereof to pass therethrough. Moreover, the one or more pocketless apertures 108 may be sized to further accommodate a hand of a user to pass through and under birthing skirt 100 to directly place and/or adjust a position of a monitor transducer MT without having to expose the patient's groin region.

In an embodiment where the one or more pocketless apertures 108 are sized to accommodate a cable of a monitor transducer MT, but not monitor transducer MT, the cable of monitor transducer MT may be routed through the one or more pocketless apertures 108 prior to or after a user puts on birthing skirt 100. In such an instance, although a medical attendant would not be able to pass a hand through the tubular portion, at least the transducer(s) may be substantially held in place and the medical attendant would be able to either slide the transducer(s) around through using a hand on top of the tubular portion, or the attendant could pull down the tubular portion from the top and adjust the transducer(s) still without exposing the patient's groin region.

Additionally, the one or more pocketless apertures 108 may be substantially closed by applying a mechanical fastener 110a, 110b. For example, a mechanical fastener 110a, 110b such as button snaps, zippers, hook and loop material fasteners, buttons and buttonholes, lace ties, drawstring, etc. may be used to close the one or more pocketless apertures 108 when not being accessed.

In an embodiment, the one or more pocketless apertures 108 may be formed along the seam at the union between tubular portion 104 and skirt portion 102. Additionally, and/or alternatively, a slit forming a pocketless aperture may be cut directly into one of the tubular portion or the skirt portion (not shown) at a location where the position of the transducer may be adjusted. In such an instance, edges of the slit may be reinforced by stitching or additional material, and the slit may be closed in a manner similar with mechanical fasteners like those depicted in FIG. 1.

Figure 2:
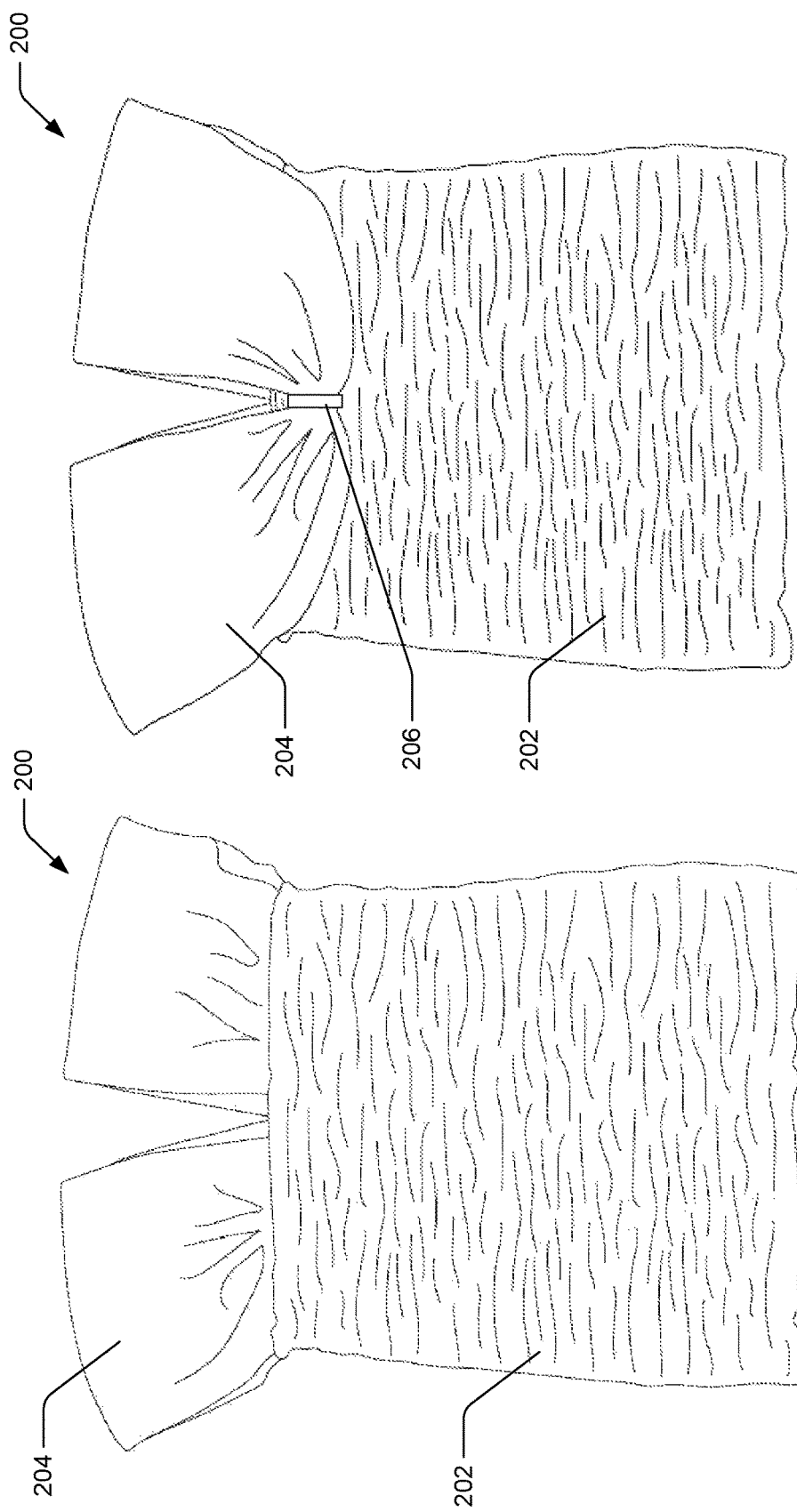
FIG. 2A illustrates a front view of a birthing garment top according to an embodiment of the instant application.
FIG. 2B illustrates a rear view of a birthing garment top according to an embodiment of the instant application.

In FIGS. 2A and 2B, a front and a back view of a birthing garment top 200 are depicted, respectively. Birthing garment top 200 includes a shape-conforming, elastic tubular section 202 to cover the birthing mother's chest region. Further, birthing garment top 200 may additionally include a shawl 204 to provide additional modesty and/or warmth.

Tubular section 202 may be formed of the same material as tubular portion 104 of birthing skirt 100, (e.g., nylon and spandex, or other elastic, latex-free material). As depicted, tubular section 202 may be sleeveless, which may facilitate the user in putting it on over the user's chest. However, it is contemplated that a tubular section may have sleeves (not shown), if desired. The length of tubular section 202 may be a length that extends over a birthing mother's breasts and toward her abdomen. Indeed, tubular section 202 may extend from under the mother's armpit to cover the breasts and abut or even overlap tubular portion 104 of birthing skirt 100. As such, the length of tubular section 202 may vary. Also, in order to provide for skin to skin contact between the mother and a newborn child, although shape-conforming to a mother's upper body, tubular section 202 may further stretch to allow for her upper torso, and for her newborn baby to be inserted between tubular section 202 and the mother's chest region. Tubular section 202 may thus provide additional safety for the newborn by "hugging" and drawing the newborn close to the mother and eliminating the risk of slipping from the mother's skin and grasp. The elastic nature of tubular section 202 also facilitates quick access to the mother's breast to allow the baby to begin breastfeeding. By so doing, the tubular section 202 may provide benefits to a newborn by providing an easier to use, safer, and more discrete article that facilitates skin to skin contact between the mother and the newborn child. This is especially useful given the abundance of scientific evidence that newborns born at or around term that do not exhibit abnormal psychological symptoms who are placed skin to skin with their mothers immediately or near immediately after birth may make the transition from fetal to newborn life with greater respiratory, temperature, and glucose stability and less crying, which may indicate decreased stress on the newborn.

In the front view shown in FIG. 2A of birthing garment top 200, shawl 204 appears to be shoulder straps that extend from a back side of birthing garment top 200. However, shawl 204 may extend lengthwise down one or both sides of the user's chest (see FIG. 3), or as depicted in FIG. 2A, opposing ends of shawl 204 may be tucked into tubular section 202. Note, when shawl 204 is not tucked into tubular section 202, a length thereof may hang to cover the patient's breast when breastfeeding. Moreover, shawl 204 may be a strip of material having a length dimension longer than a perimeter dimension of an opening of the tubular section 202.

Additionally, birthing garment top 200 may include a fastener 206, such as a loop connected to a back side of tubular section 202, as seen in FIG. 2B. Fastener 206 permits the user to removably attach shawl 204 to tubular section 202 by inserting shawl 204 into fastener 206 and pulling shawl 204 partway through fastener 206. Accordingly, a user may remove shawl 204 if desired for any reason. Any one of other mechanical fasteners, such as those described herein may be used instead of a loop for fastener 206. For example, fastener 206 may be a button snap, hook and loop material fastener, button and buttonhole, lace tie, etc.

In an embodiment shown in FIG. 3, an obstetric apparel kit 300 is depicted. Apparel kit 300 may include both a birthing skirt 302 and a birthing garment top 304. As shown, birthing skirt 302 may include at least two pocketless apertures 306a and 306b disposed on opposite sides of birthing skirt 302, whereby the separation may facilitate distinction between a fetal monitor transducer inserted in one aperture and a contraction monitor transducer inserted into the other aperture (not depicted). Notably, birthing skirt 302 and birthing garment top 304 may be two distinct pieces, as indicated by gap 308. Thus, as distinct pieces, apparel kit 300 provides the ability to preserve privacy to some extent on both the upper body and the lower body, even when adjustments are being made to the transducer positions.

Conclusion

Although several embodiments have been described in language specific to structural features and/or methodological acts, it is to be understood that the claims are not necessarily limited to the specific features or acts described. Rather, the specific features and acts are disclosed as illustrative forms of implementing the claimed subject matter.

What is claimed is:

1. An article of apparel, comprising: a birthing skirt including:
    a skirt portion comprising a waist opening, the skirt portion having a length configured to extend below a waist of a user and cover at least a groin of the user;
    a tubular portion comprised of a shape-conforming and elastic material and comprising a bottom end and a top end, the bottom end of the tubular portion attached to the waist opening of the skirt portion and extending to the top end such that, when the birthing skirt is worn by the user, the tubular portion is configured to extend from the top end of the tubular portion proximate breasts of a user to cover an abdomen of the user: and
    a pocketless aperture through a side of the birthing skirt, the pocketless aperture fixedly attached to the birthing skirt and sized to accommodate a width of at least one of a fetal monitor, a contraction monitor, or a cable of a monitor, wherein the at least one fetal monitor or the contraction monitor is held in place on the abdomen of the user by the tubular portion when positioned beneath the tubular portion;
    further comprising a birthing garment top including a sleeveless tubular section, wherein the sleeveless tubular section is formed of a shape-conforming and elastic material having an elasticity to accommodate an upper torso of the user and at least one baby therein; wherein the birthing garment top further includes a shawl sized to wrap around a user's shoulders and an upper torso of the user, the shawl including a strip of material having a length dimension longer than a perimeter dimension of an opening of the tubular section.

2. The article of apparel according to claim 1, wherein the pocketless aperture is a first pocketless aperture, and the birthing skirt further comprises:
    a second pocketless aperture through the side of the birthing skirt, the first pocketless aperture and the second pocketless aperture spaced apart from each other.

3. The article of apparel according to claim 1, wherein the pocketless aperture is one of: a gap in a seam between the skirt portion and the tubular portion, a slit through the tubular portion, or a slit through the skirt portion.

4. The article of apparel according to claim 1, wherein the pocketless aperture is closable via one or more of: a hook and loop fastener, a button snap, a button and buttonhole, a zipper, a lace, or a drawstring.

5. The article of apparel according to claim 1, wherein the waist opening includes an elastic material.

6. The article of apparel according to claim 1, wherein the tubular section includes a loop fixed to an external side of the tubular section of the birthing garment top, and wherein the shawl is removably attachable to the tubular section by inserting an end of the shawl through the loop.

7. An apparel kit, comprising: a birthing skirt including:
a skirt portion comprising a waist opening, the skirt portion having a length configured to extend below a waist of a user and cover at least a groin of the user;
a tubular portion comprised of a shape-conforming and elastic material and having comprising a bottom end and a top end, the bottom end of the tubular portion attached to the waist opening of the skirt portion and extending to the top end such that, when the birthing skirt is worn by the user, the tubular portion is configured to extend from the top end of the tubular portion proximate breasts of the user to cover an abdomen of the user;
a pocketless aperture through a side of the birthing skirt, the pocketless aperture fixedly attached to the birthing skirt and sized to accommodate a width of at least one of a fetal monitor, a contraction monitor, or a cable of a monitor, wherein the at least one of the fetal monitor or the contraction monitor is held in place on the abdomen of the user by the tubular portion when positioned beneath the tubular portion; and
a birthing garment top including a tubular section sized to accommodate a torso of the user, the birthing garment top formed of a shape-conforming and elastic material; further comprising a shawl sized to wrap around a back of the user and across shoulders of the user and extend over chest of the user across at least a portion of the tubular section when the user is wearing the tubular section; wherein the sleeveless tubular section is formed of a shape-conforming and elastic material having an elasticity to accommodate an upper torso of the user and at least one baby therein; wherein the birthing garment top further includes a shawl sized to wrap around a user's shoulders and an upper torso of the user, the shawl including a strip of material having a length dimension longer than a perimeter dimension of an opening of the tubular section.

8. The apparel kit according to claim 7, wherein the material of the tubular section of the birthing garment top is a same material as the material of the tubular portion of the birthing skirt.

9. The apparel kit according to claim 7, wherein the pocketless aperture is sized to allow at least one of the fetal monitor, the contraction monitor, or the cable of the monitor to pass therethrough.

10. The apparel kit according to claim 7, wherein one or both of the tubular portion of the birthing skirt or the tubular section of the birthing garment top includes a split line through a length thereof, the split line being a separable and reconnectable joint.

11. A maternity birthing article of apparel, comprising: a lower body piece including: a skirt portion formed of stretchable, knit material;
a tubular bottom portion that is attached to a skirt, the tubular bottom portion formed of a shape-conforming and elastic material and including a bottom end and a top end, the bottom end of the tubular portion attached to the skirt portion and extending to the top end such that, when the birthing skirt is worn by the user, the tubular portion is configured to extend from the top end of the tubular portion proximate breasts of a user to cover an abdomen of the user, and when at least one of a fetal monitor or a contraction monitor is positioned beneath the tubular portion covering the abdomen, the fetal monitor or the contraction monitor is held in place on the abdomen by the tubular portion, a first closeable slit through a first side of the lower body piece; and a second closeable slit through a second side of the lower body piece, wherein the first slit and the second slit are fixedly attached to the skirt portion and sized to allow passage of at least one of the fetal monitor, the contraction monitor, or a cable of a monitor to reach beneath the tubular portion;
wherein the first slit and the second slit are disposed along a seam between the tubular bottom portion and the skirt; further comprising an upper body piece including:
a tubular top portion formed of the shape-conforming, elastic material and a shawl that is attachable to the tubular top portion.

12. The maternity birthing article of apparel according to claim 11, wherein the lower body piece includes a latex-free material.

13. The maternity birthing article of apparel according to claim 11, wherein the shawl is attachable to the tubular top portion via one of: a loop, a hook and loop fastener, a button snap, or a button and buttonhole.

14. The maternity birthing article of apparel according to claim 11, further comprising:
a first fastening member on a lower edge of the tubular bottom portion at the first slit; and
a second fastening member on an upper edge of the skirt at the first slit, wherein the first slit is closable via engagement between the first fastening member and the second fastening member.

* * * * *